United States Patent
Keifer

(10) Patent No.: US 6,769,432 B1
(45) Date of Patent: Aug. 3, 2004

(54) METHOD AND APPARATUS FOR NON-ABRASIVE CUSHIONING SEAL OF ASSISTED BREATHING DEVICES

(75) Inventor: Elizabeth Anne Keifer, San Jose, CA (US)

(73) Assignee: Hamilton Medical, Inc., Reno, NV (US)

( * ) Notice: Subject to any disclaimer, the term of this patent is extended or adjusted under 35 U.S.C. 154(b) by 0 days.

(21) Appl. No.: 10/120,928

(22) Filed: Apr. 10, 2002

(51) Int. Cl.[7] .................. A61M 16/00; A61M 15/08
(52) U.S. Cl. ..................... 128/206.11; 128/207.18; 128/200.26
(58) Field of Search .............. 128/200.24, 207.18, 128/206.11, 203.18, 203.22, 858, 200.26

(56) References Cited

U.S. PATENT DOCUMENTS

| 718,785 | A | * | 1/1903 | McNary | 128/207.18 |
| 2,265,387 | A | * | 12/1941 | McMillin | 128/207.18 |
| 3,017,882 | A | * | 1/1962 | Lewis | 128/203.22 |
| D237,219 | S | | 10/1975 | Kattwinkel | |
| 4,782,832 | A | * | 11/1988 | Trimble et al. | 128/207.18 |
| D300,962 | S | | 5/1989 | Johnson | |
| 5,513,635 | A | | 5/1996 | Bedi | |
| 5,535,739 | A | * | 7/1996 | Rapoport et al. | 128/204.23 |
| 5,724,965 | A | * | 3/1998 | Handke et al. | 128/207.13 |
| 5,752,510 | A | * | 5/1998 | Goldstein | 128/207.18 |
| 5,975,077 | A | * | 11/1999 | Hofstetter et al. | 128/204.24 |
| 6,012,455 | A | * | 1/2000 | Goldstein | 128/207.18 |
| 6,439,230 | B1 | | 8/2002 | Gunaratnam et al. | |
| 2002/0096178 | A1 | * | 7/2002 | Ziaee | 128/207.18 |

* cited by examiner

Primary Examiner—Henry Bennett
Assistant Examiner—Mital Patel
(74) Attorney, Agent, or Firm—Bernhard Kreten

(57) ABSTRACT

A method and apparatus for preventing abrasion on an infant's nose and adjacent areas when used in conjunction with respiratory administration devices.

5 Claims, 3 Drawing Sheets

METHOD AND APPARATUS FOR NON-ABRASIVE CUSHIONING SEAL OF ASSISTED BREATHING DEVICES

FIELD OF THE INVENTION

The following invention is generally related to instrumentalities and methodologies in assisted breathing in infants. More specifically, the instant invention is directed to a method and apparatus for providing a non-abrasive cushioning seal between an assisted breathing device and an infant's skin.

BACKGROUND OF THE INVENTION

Babies born prematurely frequently lack the ability to keep their lungs from collapsing. Under normal circumstances, a baby's lungs will expand during inhalation and only partially contract during exhalation. Premature or newborn babies frequently have weak inspiratory movements causing collapse of the lung after exhalation. Collapse may also occur in the newborn as a result of blockage of bronchioles by mucus or from failure of the lung to distend.

As a result, such babies are aided in breathing by an apparatus whose purpose it is to prevent lung collapse. The connection from the respiratory apparatus to the infant is embodied in a nosepiece that is inserted into the baby's nares to direct the flow of air. Because the premature infant's skin is delicate, it is susceptible to abrasions and ulcerations from the nosepiece or from other interfaces, such as masks, rendering long-term aid difficult and painful and compounding the baby's problems.

SUMMARY OF THE INVENTION

The present invention is distinguishable over the prior art in that abrasion of an infant's nose is avoided while the infant is receiving assisted breathing support. Preferably, a silicone rubber nostril piece is provided with a foam pad that serves as a buffer between the infant's skin and the nostril piece. The foam pad has a self-adhesive backing to ensure that the pad remains securely attached to the nostril piece, and is dimensioned to surround the flexible stems that provide the infant with air without blocking airflow. Additionally, the pad provides protection for areas adjacent to the nose.

OBJECTS OF THE INVENTION

Accordingly, it is a primary object of the present invention to provide a new and novel device and method for assuring that an infant's nostril piece remains in place as long as necessary.

It is a further object of the present invention to provide a device and method as characterized above in which abrasion of the infant's skin adjacent the nares is avoided.

It is a further object of the present invention to provide a device and method as characterized above which is easy to apply and to replace.

Viewed from a first vantage point, it is an object of the present invention to provide a device to prevent abrasion on the nose of an infant receiving assisted breathing, comprising, in combination: two nostril-engaging stems, dimensioned to be received within the nares of the infant; and friction-reducing means circumscribing the nostril-engaging stems and abutting the nose of the infant.

Viewed from a second vantage point, it is an object of the present invention to provide a nose abrasion kit for an infant including a nostril-engaging member dimensioned to penetrate nares of the infant, and an adhesive-backed foam member dimensioned to overlie the nostril-engaging member and abut against a nose of the infant.

Viewed from a third vantage point, it is an object of the present invention to provide a method for reducing nose friction on an infant undergoing respiratory control, the steps including: interposing a low friction pad between an infant nose and a respiratory administering device.

These and other objects will be made manifest when considering the following detailed specification when taken in conjunction with the appended drawing figures.

DESCRIPTION OF PREFERRED EMBODIMENTS

Figure 4:
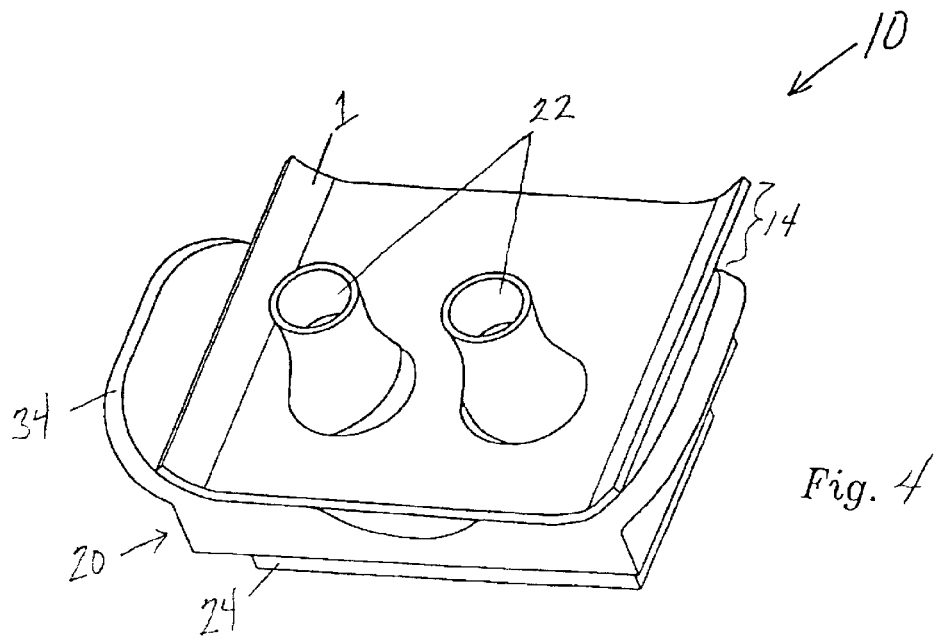
FIG. 4 is a top perspective view of the nostril piece with the sealing insert in place.

Considering the drawings, wherein like reference numerals denote like parts throughout the various drawing figures, reference numeral 10 as shown in FIG. 4 is directed to the non-abrasive cushioning device according to the present invention.

Figure 1:
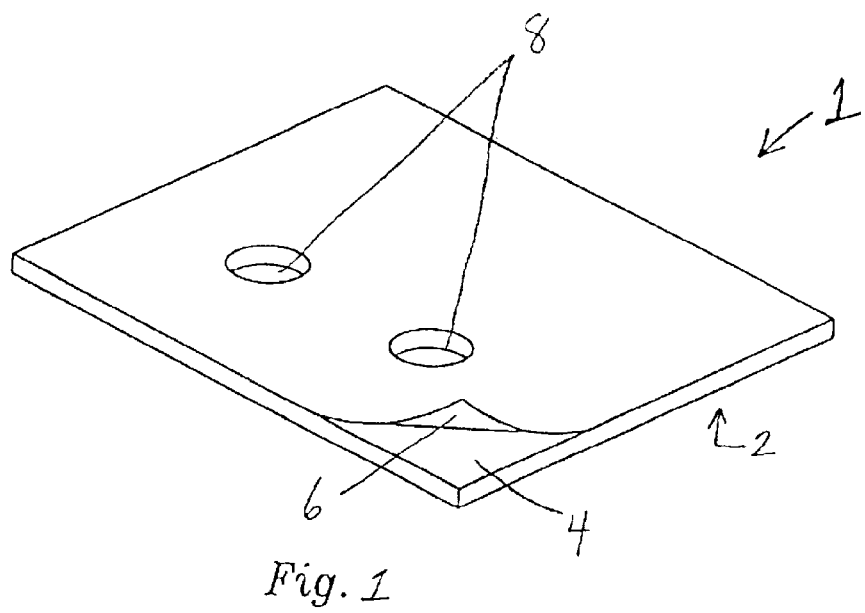
FIG. 1 is a perspective view of the sealing insert of the present invention.

In its essence, the non-abrasive cushioning device 10 is formed by joining a cusion layer 1 with a nostril piece 20. The cushion layer 1 is formed as a thin sheet of material, preferably low-density polyethylene foam, having a foam side 2 and an adhesive side 4 (FIG. 1). The adhesive side 4 is preferably coated with an acrylic adhesive, and formed with a peel-off backing 6. The cushion layer 1 is equipped with two ports 8 that register with a nostril piece 20, preferably made of silicone rubber, allowing the nares-receiving stems 22 of the nostril piece 20 to pass through the ports 8. As show, the ports 8 may be located off-center with respect to the short axis of the cushion layer 1, to provide additional cushioning to adjacent areas when the non-abrasive cushioning device 10 is assembled.

Figure 2:
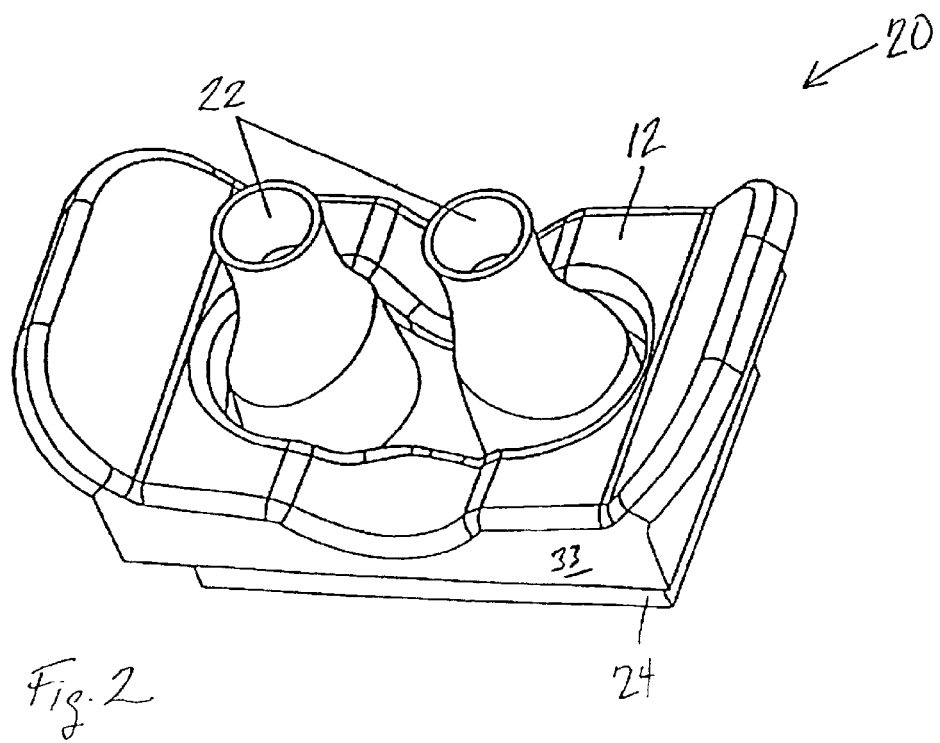
FIG. 2 is a top perspective view of the nostril piece of the present invention.
Figure 3:
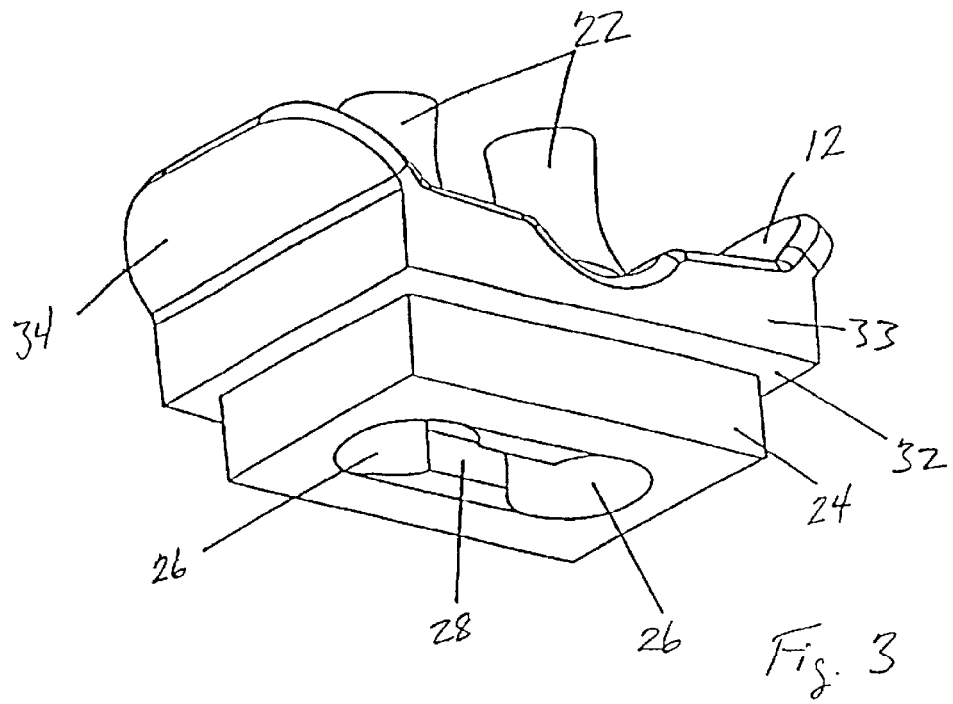
FIG. 3 is a bottom perspective view of the nostril piece of the present invention.

The nostril piece 20 (FIGS. 2,3) fits an apparatus such as that disclosed in U.S. Pat. No. 5,975,077. Block 24 on a bottom face of the nostril piece 20 includes openings 26 to frictionally override an outer periphery of an air delivery apparatus (not shown) in tight, sealing engagement. A relief 28 extends between the openings 26, serving to equalize airflow between the nares.

Figure 5:
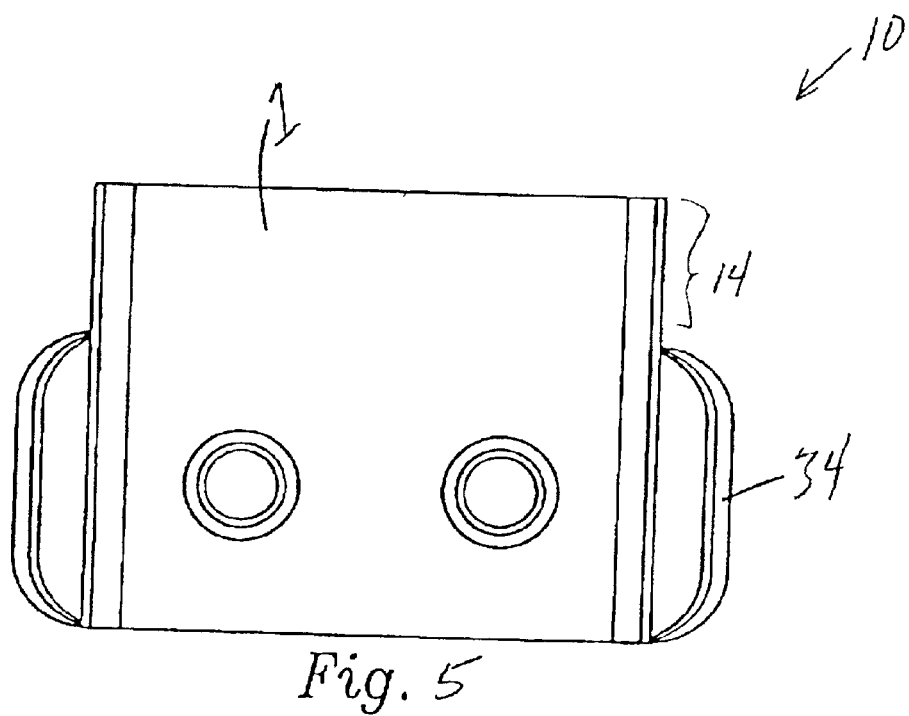
FIG. 5 is a top view of the nostril piece with the sealing insert in place.
Figure 6:
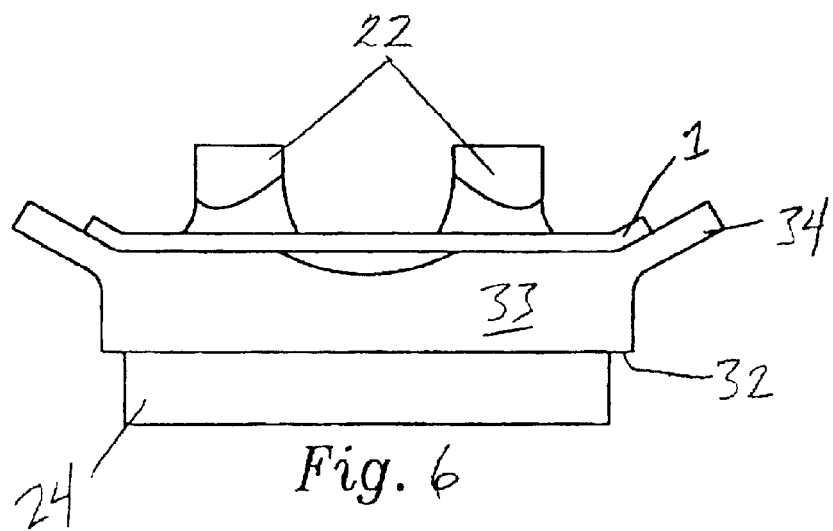
FIG. 6 is a side view of the nostril piece with the sealing insert in place.

A side 12 of the nostril piece 20 opposite the block 24 includes a pair of nares receiving stems 22, hollow and in fluid communication with the openings 26 and therefore the air delivery apparatus. A ledge 32 of the nostril piece 20 includes a peripheral wall 33 which ensures no air leakage at the connection site. The upper wall 33 of the ledge 32 includes extended ends 34 for removal of the nostril piece from the attached air delivery apparatus. The cushion layer 1 covers the upper surface of the ledge 32. FIGS. 4–6 show the nostril piece 20 with the cushion layer 1 in place.

In use and operation, the backing 6 is removed from the cushion layer 1 and the adhesive side 4 is pressed against the nostril piece 20 such that the two ports 8 overlie the nares-receiving stems 22. The adhesive side 4 bonds to the side 12 of the nostril piece 20 overlying its entire extent, leaving an overhang 14 of the cushion layer 1 that is in not attached to the nostril piece 20. The overhang 14 may serve a dual function, providing a convenient surface while installing or removing the cushion layer 1 and protecting skin adjacent to the baby's nose from abrasion. When the cushion layer 1 contacts areas around the baby's nostrils, the device 10 rides with the baby during respiratory motion and minimizes frictional abrasion between the nostril piece 20 and the baby.

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. A method for reducing nose friction on an infant undergoing respiratory control, the steps including:

forming a substantially rectangular low friction pad having two ports, said low friction pad having an adhesive backing whereby an adhesive layer is protected by a covering;

removing said covering to expose said adhesive layer; and affixing said adhesive layer of said low friction pad to a nostril piece having integrated nostril engagement means, said nostril engagement means to penetrate the nares of an infant, such that said ports register with said nostril engagement means, whereby an overhang of said pad is present adjacent to a covered surface of said nostril piece.

2. A device to prevent abrasion on the nose of an infant receiving assisted breathing comprising, in combination:

a nostril piece having
      integrated nostril engagement means for penetrating the nares of an infant,
      a contoured surface circumscribing said nostril engagement means, wherein said surface is adapted to fit near the infant's nose, and
      two ports through said nostril piece, wherein said ports run through said nostril engagement means and terminate at an opposite end of said nostril piece, wherein a terminus of said port further comprises:
         an opening between said ports, wherein said ports are connected by said opening, and whereby airflow and pressure are equally distributed in said opening; and a cushioning pad, said cushioning pad attached to said nostril piece and circumscribing said integrated nostril engagement means, whereby said cushioning pad is interposed between an infant nose and said nostril piece.

3. The device of claim 2 wherein said nostril piece further comprises:

a ledge surrounding said opening, said ledge adapted to mate with an assisted breathing device.

4. The device of claim 3 wherein said cushioning pad covers substantially all of said contoured surface.

5. The device of claim 4 wherein mating of said cushioning pad with said nostril piece exhibits an overhang of said cushioning pad.

* * * * *